United States Patent [19]

Martin et al.

[11] Patent Number: 4,661,517

[45] Date of Patent: Apr. 28, 1987

[54] SYNERGISTIC BIOCIDE OF 2-(P-HYDROXYPHENOL) GLYOXYLOHYDROXIMOYL CHLORIDE AND METHYLENE BIS THIOCYANATE

[75] Inventors: Cynthia H. Martin, Plainfield; Thomas M. LaMarre, Aurora, both of Ill.

[73] Assignee: Nalco Chemical Company, Naperville, Ill.

[21] Appl. No.: 874,926

[22] Filed: Jun. 16, 1986

[51] Int. Cl.[4] .................... A01N 33/24; A01N 47/48
[52] U.S. Cl. .................................. 514/515; 210/764; 514/640
[58] Field of Search ................................ 514/515, 640

[56] References Cited

U.S. PATENT DOCUMENTS 3,996,378  12/1976  Payton ............................... 514/516

OTHER PUBLICATIONS

C.A.; vol. 92 (1980) 92:127066f.
F. C. Kull et al., "Mixtures of Quaternary Ammonium Compounds and Long-Chain Fatty Acids as Antifungal Agents", Applied Microbiology, vol. 9, pp. 538-541, (1936).

*Primary Examiner*—Allen J. Robinson
*Attorney, Agent, or Firm*—John G. Premo; Anthony L. Cupoli; Donald G. Epple

[57] ABSTRACT

A synergistic biocide blend of 2-(p-hydroxyphenol) glyoxylohydroximoyl chloride and methylene bis thiocyanate.

4 Claims, No Drawings

SYNERGISTIC BIOCIDE OF 2-(P-HYDROXYPHENOL) GLYOXYLOHYDROXIMOYL CHLORIDE AND METHYLENE BIS THIOCYANATE

FIELD OF THE INVENTION

The present invention relates to certain processes and compositions useful for inhibiting the growth of slime in water employed for industrial purposes, particularly water employed in the manufacture of pulp and paper, water employed in cooling water systems, as well as other industrial waters.

BACKGROUND

The mechanisms by which chemical agents exert antimicrobial activity depend upon the effective contact between the chemical and the organism, and involve disruptive interactions with some biochemical or physical component of the organism, which component is essential to its structure or metabolism. The targets may be an enzyme, or enzymes, the cell membrane, an intracellular system, the cytoplasm, or any combination of these. The nature of the action of the toxicant is dependent on the organism, on the antimicrobial agent, and on the environment in which the interaction occurs. The unique composition of each toxicant implies a different mode of action.

The present invention provides superior antimicrobial activity through a synergy in which the disruptive interaction on the organism by the two toxicants together is greater than the sum of both toxicants taken alone. The synergy does not arise from the expected activity of the components or from a predictable improvement in activity. In all cases, the synergism depends largely on the interactions of the antimicrobial agents with the organism. The cellular processes are so complex as to render such synergism an unpredictable, and indeed rare, phenomenon.

SUMMARY OF THE INVENTION

The novel compositions and methods of the present invention are processes or mixtures which show unexpected synergistic activity against bacteria which are common to industrial waters and which produce slimes in aqueous systems or bodies, which slimes are objectionable from either an operational or aesthetic point of view. Specifically, the invention is directed to the use of compositions comprising a combination of 2-(p-hydroxyphenol)glyoxylohydroximoyl chloride (HGHMCl) and methlene bis thiocyanate (MBT).

More specifically, the invention comprises a synergistic biocidal composition useful in treating industrial process waters to prevent and control the growth of gram-negative bacteria which comprises from 10-90% by weight of 2-(p-hydroxyphenol)glyoxylohydroximoyl chloride (HGHMCl) from 90-10% by weight of methylene bis thiocyanate (MBT).

BACTERIA

The troublesome slimeforming bacteria in industrial process waters tend to be primarily gram-negative rod-shaped aerobes. Of this group, *Pseudomonas aeruginosa* is one of the most common and most difficult to control. The invention is capable of affording good control of *Pseudomonas aeruginosa*. It is also capable of affording control of other species of bacteria, in particular other species of gram-negative, rod-shaped aerobes of such genera as Aerobacter, Flavobacterium, Pseudomonas, for example, *Pesudomonas aeruginosa, Pseudomonas fluorescens, Pseudomonas, levanicum, Pseudomonas stutzeri, Pseudomonas maltophilia, Aerobacter, aerogenes, Aerobacter cloacae*, and others.

The Composition

When the toxicants are combined to treat bacteria, in particular, gram-negative slimeforming aeobes, they are most highly synergistic where the weight ratio of HGHMCl to MBT ranges from 90/10 to 10/90.

Dosages

For most industrial waters, an effective biocide dosage will be within the range of from 1-25 ppm as actives. The actual dosage used will depend on the water treated.

Experimental Procedure

The synergism of these components is demonstrated by adding 2-(p-hydroxyphenol)glyoxylohydroximoyl chloride (HGHMCl) and methylene bis thiocyanate (MBT) in varying ratios over a range of concentrations to sterile white water from a paper mill. The white water, adjusted to the desired pH, was inoculated with *Pseudomonas aeruginosa*, ATCC 15442.

The total count of the control was $1.8 \times 10^7$ bacteria per milliliter. The concentrations of the above toxicants were added to aliquots of the inoculated white water, and these aliquots were incubated at 37° C. for 24 hours. In this study of the control of bacterial growth, the nutrient medium for plating was tryptone glucose extract agar, poured at 50° C. into sterile Petri dishes containing the appropriate dilutions of the white water which had been inoculated and treated as described. Once the medium in these dilution plates had solidified, the plates were incubated for over forty-eight hours at 37° C. After the incubation, the results were read as growth or no growth; and the lowest concentration of each toxicant or of each ratio of the combined toxicants that prevented growth on the agar was taken as the end point. This procedure provides the toxicant with a greater challenge by testing the toxicants under conditions which approximate the conditions under which they will be used.

The end points of each of the ratios tested were compared with end points of the concentrations of the pure toxicants. Synergism was determined according to the industrially-accepted method described by S. C. Kull, P. C. Eisman, H. D. Sylwestrowicz, and R. L. Mayer in *Applied Microbiology*, Vol. 9, pages 538–541, (1936), which is herein included as reference.

As regards the Kull et al. document, the data here presented can be described as follows:

$Q_A$ = the ppm of actives of HGHMCl alone which produced an endpoint $Q_a$ = the ppm of actives of HGHMCl, in combination, which produced an endpont $Q_B$ = the ppm of actives of MBT alone which produced an endpoint $Q_b$ = the ppm of actives of MBT, in combination, which produced an endpoint $$\text{if } \frac{Q_a}{Q_A} + \frac{Q_b}{Q_B} \begin{cases} < 1 \text{ indicates synergy} \\ > 1 \text{ indicates antagonism} \\ = 1 \text{ indicates additivity} \end{cases}$$

Ratios of HGHMCl/MBT: 100/0, 0/100, 90/10, 10/90, 75/25, 25/75, 50/50.

Concentrations tested for each ratio in terms of parts per million of actives: 0.3, 0.6, 1.0, 1.5, 3.0, 5.0, 7.5, 10, 20, 30, 40, 50, 60.

The above test method is reproduceable and is a good method for determining the range of synergism existing against candidate biocides being screened for application in the treatment of biologically contaminated industrial waters. The efficacy and validity of this test method is discussed in the Appendix which appears hereafter. In order to present the following test results as clearly as possible, the Appendix also contains the calculations used to produce the test results set forth in Table I. The effectiveness of combinations of HGHMCl and MBT are set forth below in Table I.

TABLE I

SYNERGISM STUDY FOR COMBINATION BIOCIDES AGAINST BACTERIA

Growth: +
No Growth: −
Control Culture: $1.36 \times 10^8$ organism per ml

| Ratio HGHMCl/MBT | Concentrations (ppm) | | | | | | |
|---|---|---|---|---|---|---|---|
| | .3 | .6 | 1.0 | 1.5 | 3.0 | 5.0 | 7.5 |
| 100/0 | + | + | + | + | + | + | + |
| 0/100 | + | + | + | + | + | + | + |
| 90/10 | + | + | + | + | + | + | + |
| 10/90 | + | + | + | + | + | + | + |
| 75/25 | + | + | + | + | + | + | + |
| 25/75 | + | + | + | + | + | + | + |
| 50/50 | + | + | + | + | + | + | + |
| | 10 | 20 | 30 | 40 | 50 | 60 | |
| 100/0 | | + | + | + | + | − | |
| 0/100 | + | − | − | − | − | − | |
| 90/10 | + | + | + | − | − | − | |
| 10/90 | − | − | − | − | − | − | |
| 75/25 | + | + | − | − | − | − | |
| 25/75 | − | − | − | − | − | − | |
| 50/50 | − | − | − | − | − | − | |

| DGH/ISOTH Ratio | $\frac{Q_a}{Q_A} + \frac{Q_b}{Q_B}$ | Rating |
|---|---|---|
| 90/10 | 0.800 | <1 Synergy |
| 10/90 | 0.467 | <1 Synergy |
| 75/25 | 0.825 | <1 Synergy |
| 25/75 | 0.417 | <1 Synergy |
| 50/50 | 0.333 | <1 Synergy |

ANTAGONISTIC COMBINATIONS

The two components of the present invention were tested singly with a variety of other toxicants, using the methods described above; as is expected, most such combinations are antagonistic or merely additive. An example is presented below in order to better show the nature of such testing.

The mixture of 2-(p-hydroxyphenol)-glyoxylohydroximoyl chloride (HGHMC1) was found to be antagonistic in combination with a blend of quaternary amines (QUAT), in a test against bacteria.

| Ratio HGHMCl/QUAT | Endpoint (ppm actives) | $\frac{Q_a}{Q_A} + \frac{Q_b}{Q_B}$ | Rating |
|---|---|---|---|
| 100/0 | 20 | 1.00 | |
| 0/100 | 30 | 1.00 | |
| 90/10 | 40 | 1.93 | Antagonistic |
| 10/90 | 20 | 0.70 | Synergistic |
| 75/25 | 60 | 2.75 | Antagonistic |
| 25/75 | 30 | 1.13 | Antagonistic |
| 50/50 | 70 | 2.92 | Antagonistic |

APPENDIX

Discussion

The conventional presentation of a test of synergy demands that the data be presented in terms of growth or no growth. The convention has the merit of presenting the data simply and directly in terms that make the calculation of synergy straightforward. This presentation may, however, require a thorough explanation of the factors which are taken into account in the determination of the endpoints of the test. The determination of synergy demands wholly on these endpoints.

The data presented in Table I demonstrate synergy, but may require explanation. First, the indication of growth (+) in Table I is heavy growth. No growth (−) indicates no growth on a zero-dilution plate, on a one-dilution plate, and on a two dilution plate. The zero-dilution plate will show as few as one bacterial colony per milliliter; the lowest count on a one-dilution plate is ten bacteria per milliliter, and the two-dilution plate shows a bacterial count greater than $10^2$ bacteria per milliliter. In short, in Table I, the difference between growth (+) and no growth (−) involves a three-log reduction in bacterial count. For example, in the case of the ratio 100/0, the bacterial count at of 50 ppm was greater than $10^2$ bacteria per milliliter. At 60 ppm, the bacterial count was below detection (less than 1 bacteria per milliliter). Therefore, the endpoint for 100/0 is taken to be 60 ppm.

The endpoint for 100/0 is, in the strictest sense, between 50 and 60 ppm. In this case, where a concentration of toxicant as high as 50 ppm is not capable of completely inhibiting growth, a three-log reduction in bacterial count is not to be expected by increasing the concentration of biocide by less than 5–10 ppm. The endpoint cannot fall closer to 50 ppm than to 60 ppm. The 10 ppm interval is indeed significant when testing toxicants with this magnitude of toxicity. Additional data points at closer intervals are unnecessary. The progression of the increments between concentrations in these experiments (0.3, 0.6, 1.0, 1.5, 3.0, 5.0, 7.5, 10, 20 . . . etc.) is standard method in producing representative microbiological data.

The same logic applies to all the endpoints of the test. The best and worst extrapolations of the data can be determined in this way. Since the endpoints of 100/0 must fall closer to 60 than to 50 ppm, and the endpoint of 0/100 must fall closer to 20 than to 10 ppm, let us say that;

$$55 < QA < 60$$

$$15 < QB < 20$$

though it is very unlikely that the endpoints would occur at the lower concentrations. Let us use the ratio 50/50 in this example. For the reasons described above, the endpoint for 50/50 must fall closer to 10 than 7.5, therefore;

$$8.75 < 50/50 < 10$$

In the worst possible case;

QA=55

QB=15

And the worst endpoint for 50/50 under these circumstances is 10 ppm. Therefore, Qa=0.5×10=5

Qb=0.5×10=5

Using the previously defined formula for the calculation of synergy the following synergistic result is determined:

$$\frac{Qa}{QA} + \frac{Qb}{QB} = 0.43$$

This formula shows the extent to which the combination of the two toxicants creates a surprising increase in activity. When the synergy ratio is less than 1, the combination is truly synergistic instead of antagonistic or merely additive. In this experiment, calculating the worst possible case for the least effective ratio, the ratio is still extremely synergistic.

In the test of synergy against bacteria, the endpoints are clearly defined, and the increase in activity presented by the combinations is well within the defined limits of synergistic activity.

This means of interpreting the data goes to show how truly representative the endpoints are. The data, as presented and calculated in Table I, are not extrapolated into the best or worst cases. Instead, the data summarize the activity shown using standard method. As mentioned above, this interpretation also depends on understanding that the difference between growth and no growth in the synergy study against bacteria involves a three-log reduction in bacterial count. These interpretations of the data confirm that the ratios of toxicants, 90/10 through 10/90, result in an unexpected amelioration of toxicity.

As the invention will be applied commercially, the entire range of weight ratios will be very important. Many different ratios will be used to provide the best control of these slimeforming bacteria with the least amount of toxicant. This more effective use of toxicants is not only of commercial interest, but also of environmental interest.

| Calculations for Table I | |
|---|---|
| $Q_A$ = ppm active $Q_B$ = ppm active | $\frac{Q_a}{Q_A} + \frac{Q_b}{Q_B}$ |
| A. 90/10 $Q_a$ = 40 ppm × .90 = 36 $Q_b$ = 40 ppm × .10 = 4 | B. 10.90 $Q_a$ = 10 ppm × .10 = 1 $Q_b$ = 10 ppm × .90 = 9 |
| $\frac{36}{60} + \frac{4}{20} = 0.800$ | $\frac{1}{60} + \frac{9}{20} = 0.467$ |
| C. 75/25 $Q_a$ = 30 ppm × 0.75 = 27 $Q_b$ = 30 ppm × 0.25 = 7.5 | D. 25/75 $Q_a$ = 10 ppm × 0.25 = 2.5 $Q_b$ = 10 ppm × 0.75 = 7.5 |
| $\frac{27}{60} + \frac{7.5}{20} = 0.825$ | $\frac{2.5}{60} + \frac{7.5}{20} = 0.417$ |
| E. 50/50 $Q_a$ = 10 ppm × 0.50 = 5 $Q_b$ = 10 ppm × 0.50 = 5 | |
| $\frac{5}{60} + \frac{5}{20} = 0.333$ | |

Having thus described the invention, it is claimed as follows:

1. A biocidal composition useful in treating industrial process waters to prevent the growth of gram-negative bacteria which comprises a synergistic mixture of 2-(p-hydroxyphenol)gloxylohydroximoyl chloride and methylene bis thiocyanate wherein the ratio of 2-(p-hydroxyphenol)glyoxyohydroximoyl chloride to methylene bis thiocyanate is within the range 90/10 to 10/90.

2. The synergistic biocidal composition of claim 1 where the gram-negative bacteria is Pseudomonas bacteria.

3. A method of controlling the growth of gram-negative bacteria of the type commonly found in industrial process waters which comprises treating said waters with a bactericidal amount of the composition of claim 1.

4. A method for controlling the growth of Pseudomonas bacteria which comprises treating said waters with a bactericidal amount of the composition of claim 1.

* * * * *